United States Patent [19]
Crisio, Jr.

[11] Patent Number: 5,302,127
[45] Date of Patent: Apr. 12, 1994

[54] DENTAL IMPLANT STRESS STABILIZER

[76] Inventor: Raymond A. Crisio, Jr., 18 S. 13th St., Belleville, Ill. 62220

[21] Appl. No.: 69,335

[22] Filed: Jun. 1, 1993

[51] Int. Cl.⁵ .................................. A61C 8/00
[52] U.S. Cl. .......................... 433/173; 433/174
[58] Field of Search ........................ 433/173, 174

[56]  References Cited
U.S. PATENT DOCUMENTS

| | | | |
|---|---|---|---|
| 3,955,280 | 5/1976 | Sneer | 433/174 |
| 4,359,318 | 11/1982 | Gittleman | 433/173 |
| 4,511,336 | 4/1985 | Hidaka et al. | 433/173 |
| 5,013,242 | 5/1991 | Prezmecky | 433/173 |

Primary Examiner—John J. Wilson
Attorney, Agent, or Firm—Robert K. Rhea

[57]  ABSTRACT

A horizontal and vertical sheer stress distributor for a dental prothesis implant is formed by a cylindrical member threadedly inserted into a jaw bone cavity. An angular disposed through bore in the root member secures an elongated bar projecting angularly downward from the root member into the jaw bone adjacent the cavity.

7 Claims, 2 Drawing Sheets

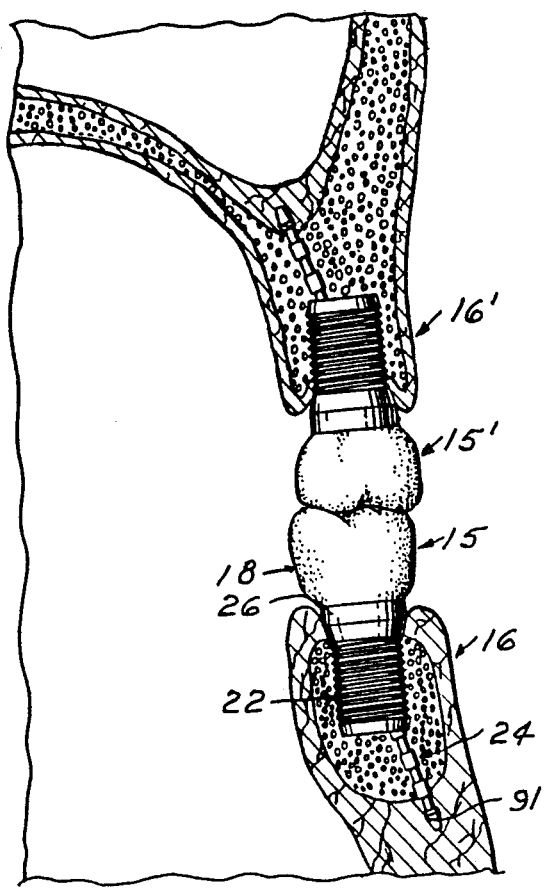
FIG. 1
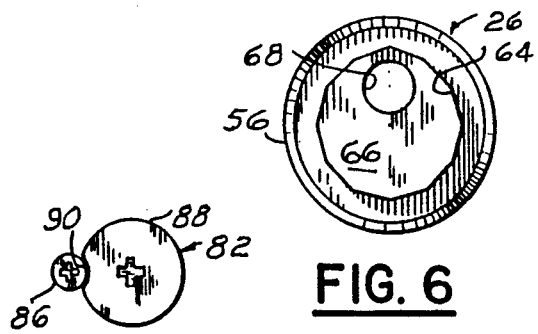
FIG. 6
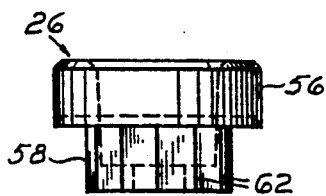
FIG. 8
FIG. 5
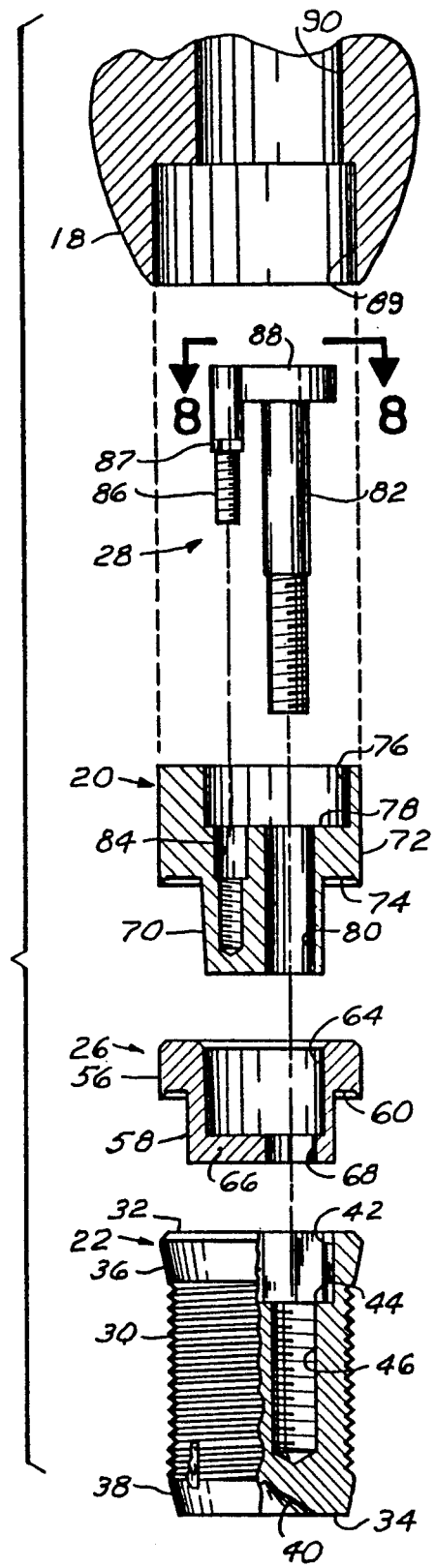
FIG. 7

DENTAL IMPLANT STRESS STABILIZER

BACKGROUND OF THE INVENTION

This invention relates to dentistry and more particularly to a dental implant having an outrigger stabilizer to preclude a larger implant movement relative to the jaw bone.

1. Field of the Invention

Dental prothesis formed of selected material are conventionally implanted and anchored in place by mechanical means such as pegs.

The use of allografts and autografts in guided tissue regeneration has greatly increased the use of dental implants. However, bone can only withstand a certain amount of stress before it fails. In current implant designs, it is believed unlikely that a single molar implant can serve for extended use with the root tip anchored in meoullary (spongy) bone.

This invention overcomes this difficulty by spreading the horizontal and sheer stress from ankylose implants throughout more bone area than conventional single cylinder dental prothesis.

2. Description of the Prior Art

U.S. Pat. No. 4,511,366 issued Apr. 16, 1985 to Hidaka et al for ARTIFICIAL APPETITE DENTAL ROOT discloses a generally cylindrical dental implant having a generally hexagonal-shaped step diameter inwardly projecting end portion in which the larger diameter portions are wedged against a solid bone portion of the jaw to provide circumferential spaces around the reduced diameter portions between the larger diameter portions for inducing osseous labyrinth bone growth.

U.S. Pat. No. 4,359,318 issued Nov. 16, 1982 to Gittleman for DENTAL IMPLANT discloses anchoring a dental implant by using a drill bit similar to a hole saw for forming an annular socket in the osseous bone around a centrally bored upstanding stump for receiving a complimentary sized foraminated annular wall implant. An electrode is mounted in the stump bore and connected with a battery to apply electrical current to the electrode and induce bone apposition in the stump and bone tissue to knit through wall apertures in the sleeve implant.

This invention is believed distinctive over these patents by a die-threaded tooth implant having an outward and downwardly inclined stress bar for transferring horizontal and sheer stress from ankylose implants to establish a healthy osseointegrated interface between the implant and bone by preventing stress overload.

SUMMARY OF THE INVENTION

This tooth implant may be fitted in either an extraction site before bone modeling occurs or in a drilled hole.

The implant includes a cylindrical externally die-threaded roof or base member which is screwed into the bore hole and provided with an angularly disposed bore for receiving a downwardly and outwardly inclined stress relief bar.

A cup-like adapter or abutment is interposed between a lug-type wax tooth base assembly which supports an anchor screw extending through the tooth base into the base member.

The principal object of this invention is to provide a tooth implant which includes a stress relief bar for spreading the sheer and horizontal stress during mastification to bone area remote from the position of the implant and enhance the longevity of the implant.

BRIEF DESCRIPTION OF THE DRAWINGS

FIG. 1 is a fragmentary vertical cross sectional view, partially in elevation, illustrating upper and lower molar implants;

FIG. 5 is a side elevational view of tooth implant abutment;

FIG. 6 is a top view of FIG. 5;

FIG. 7 is an exploded perspective view, partially in section, of the tooth plant components, excluding the stress relief bar;

FIG. 8 is a top view taken substantially along the line 8—8 of FIG. 7; and,

DESCRIPTION OF THE PREFERRED EMBODIMENTS

Figure 2:
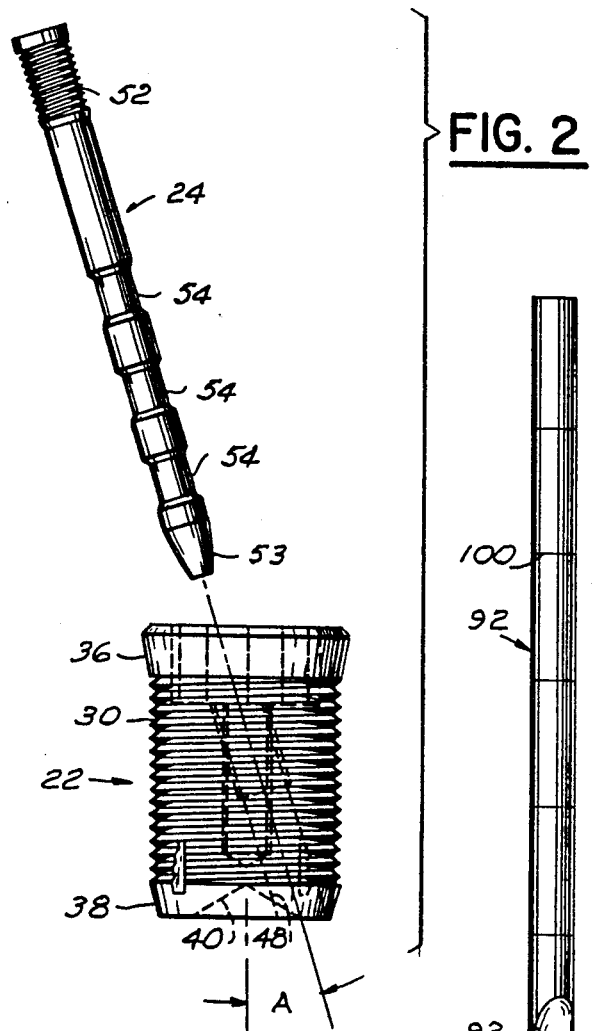
FIG. 2 is an exploded side view of the base implant and stress stabilizing bar.

Like characters of reference designate like parts in those figures of the drawings in which they occur.

In the drawings:

Referring first to FIG. 1, the reference numerals 15 and 15' respectively indicate molar implants secured in a patients mandibular and maxillary jaw 16 and 16', respectively. Since the implants 15 and 15' are identical, only the implant 15 will be described in detail, in the interest of brevity.

The molar tooth implant 15 comprises a dental prothesis such as a molar tooth 18 cast on a prothesis base 20 (FIG. 7) secured to a tooth implant root 22, having a stress relief bar 24, through a tooth implant abutment 26 (FIG. 7) by screws 28. The implant root 22 is right circular cylindrical in overall configuration having external die threads 30 intermediate its ends 32 and 34.

The top end portion 36 converges toward the threads and its depending end portion 38 converges toward its longitudinal axis.

The depending end surface 34 is provided with a substantially conical inwardly directed recess 40 for inducing trabecular bone growth to stabilize the implant during the healing stage.

The upper end surface 32 is centrally bored a selected depth to form an upwardly open socket 42 having a substantially planar bottom surface 34. The inner wall defining the socket 42 is characterized by a plurality of wrench flats (12 point) for receiving a wrench driver, not shown, for angularly rotating the implant root 22, as hereinafter described.

The root 22 is provided with an eccentric threaded bore 36 of a selected depth for receiving an anchor screw, as presently described. The root 22 is further provided with an eccentric laterally downward and directed stress bar bore 48 inclined on an angle A substantially 17½ degrees with respect to the longitudinal axis of the implant root 22 for receiving the stress bar 24. The upper end portion of the stress bar bore 48 is counterbored and threaded, as at 50, for cooperatively receiving the threads 52 on the stress bar 24.

Obviously the stress bar 24 must be fabricated in a plurality of different lengths for use of an optimum length bar with a respective implant. In the example illustrated the bar 24 terminates in a truncated conical end portion 53 and is substantially twice the length of the root implant 22. The major portion of its depending end is provided with a series of reduced diameter portions 54 for inducing bone growth and stabilizing the root implant 22 during the healing process. The purpose of the stress bar 24 is to disburse the stresses imparted to the root 22 to a remote portion of the jaw bone during mastication of food.

The abutment member 26, which is interposed between the cast tooth 18 and the root implant 22, is cylindrical cup-like in general configuration defined by an annular outstanding flange 56 at its upper limit, diametrically equal with the root 22 and greater than its stem portion 58, defining a downwardly overhanging shoulder provided with a recess 60 cooperatively nesting the upper chamfered end of the root 22 when placed within its socket 42. The periphery of the stem 58 is similarly provided with wrench flats (12 point) which are cooperatively received by the wrench flats in the root socket 42.

The upwardly open cup 64 of the abutment 26 defines a bottom wall 66 and an inner wall surface which is similarly provided with wrench flats (12 points) for receiving a socket wrench, not shown, and angular rotation of the abutment and the root implant 22 as a unit, as hereinafter described.

The implant bottom wall 66 is similarly provided with an eccentric bore 68 for coaxial alignment with the root threaded bore 46, as hereinafter described.

The wax tooth base former 20 is substantially step diameter cylindrical in overall configuration in which its substantially one half length stem 70 is circumferentially and longitudinally dimensioned to be snugly received by the abutment upwardly open socket 64.

The larger flanged end portion 72 of the tooth base former 20 is substantially diametrically equal with the diameter of the abutment 26 and is similarly provided with a downwardly facing flange shoulder recessed, as at 74, for snugly receiving the chamfered upper end of the abutment 26 when axially placed therein.

The tooth base former 20 is similarly eccentrically provided with an upwardly open cylindrical bore or recess 76 having a substantially flat bottom end 78 having an eccentric through bore 80 for coaxial alignment with the abutment bore 68 and the root implant bore 46 for receiving one of the anchor screw 82 as hereinafter explained.

A second blind threaded bore 84, in the base former 20 receives the lock screw 86 of the screws 28. The larger screw 82 has a cylindrical head 88 provided with a recess 90 in its periphery (FIG. 8) for receiving a peripheral portion of the head of the lock screw 86 for locking the larger screw 82 against an angular screw loosening rotation, for the reasons believed obvious.

The base former 20 provides a lab technician with a base to wax the cast tooth 18 thereon, in the lost wax process, wherein the base former 20 flange 72 forms a cylindrical downwardly open recess 88 in the tooth 18, when cast and an upwardly open access hole 90 eccentric with respect to the cast tooth recess 88.

OPERATION

As mentioned hereinabove the root implant 22 is inserted into an extraction site or a hole bored for that purpose. This is accomplished by inserting the depending tapered end 38 into the bore hole and utilizing a 12 point wrench drive in the recess 42 for angularly rotating the root member 22 about its longitudinally axis so that its die threads 30 progressively form cooperating threads in the jaw bone until the top end surface 32 is disposed al a desired elevation relative to the jaw bone.

Alternatively, the implant member 26 may be inserted into the 12 point recess 42 and a smaller size wrench drive utilized in rotating implant 26 assembled with the root member 22.

The stress bar aperture or bore hole 48 is positioned by the clinician to avoid alveolar nerves and achieve the optimum anchorage for the stress bar 24. The stress bar hole 91 (FIG. 1) is then drilled into the jaw bone in which a stent should preferably be used for proper guide of the drills. The stress bar 24, preferably engages the apical cortical plate in order to act as a relief valve in spreading sheer and horizontal stress during mastication.

Figures 9, 10, 11, 12:
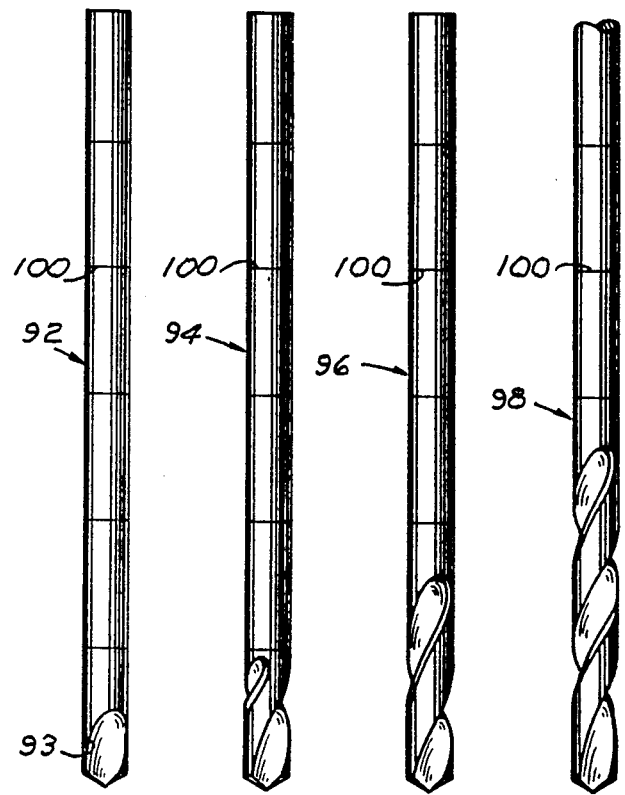
FIGS. 9, 10, 11 and 12 are side elevational views, respectively, of drill bits necessary for installing the tooth implant stress relief bar.
Figure 4:
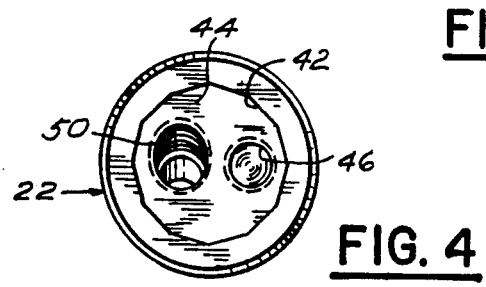
FIG. 4 is a top view of FIG. 3.
Figure 3:
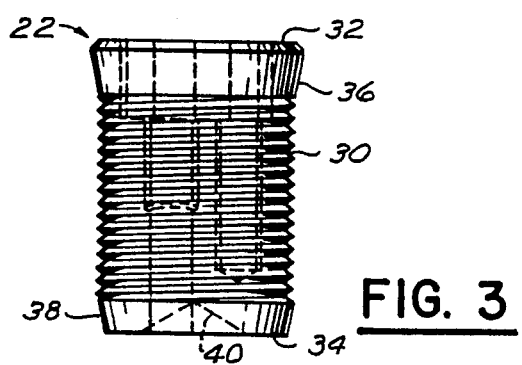
FIG. 3 is a side elevational view of the base member, per se.

Referring also to FIGS. 9, 10, 11 and 12, the respective drills illustrate four drills respectively indicated by the numerals 92, 94, 96 and 98 each having measurement rings 100 equally spaced, for example 5 mm, longitudinally thereon to enable the clinician to accurately gage the depth of the stress bar bore hole 91 being formed in the jaw through the root bore 48.

The root bore 48 forms a stent for guiding the drill 92 having the shorter flute 93 when connected with a handpiece, not shown, and first inserted through the implant roost 22. After starting the jaw flute bore hole 91 with the drill bit 92 it is removed and the bore hole cleansed prior to using the next longer flute drill bit 94. This action is repeated with the drill bits 96 and 98 until optimum depth for the stress bar 24 has been achieved.

It is preferred that the radiographic method of obtaining a three-dimensional measurement be utilized in which the multi-planar reformatted commuted tomography is provided with one millimeter non-overlapping frames which reveal the quality of both cancellous and cortical bone at selected implant sites.

After the stress bar hole 91 depth has been achieved and has been cleaned, the stress bar 24 is inserted through the root member 22 and tightened by angular rotation to engage its threads 52 with the stress bore hole threads 50.

The cast tooth 18 containing the tooth base former 20 and screws 28 is then axially placed on the abutment 26 by inserting the tooth former base stem 70 into its socket 64. The large screw 82 is then tightened in the threaded bore hole 46 of the root 22 and positioned so that the lock screw 86 with its lock washer 87 may be inserted into the threaded bore hole 84 of the tooth base former.

Thereafter the cast tooth top opening 90 is filled with conventional tooth color composite to complete the installation.

Obviously the invention is susceptible to changes or alterations without defeating its practicability. Therefore, I do not wish to be confined to the preferred embodiment shown in the drawings and described herein.

I claim:

1. A dental implant for a prothesis, comprising:
   a substantially cylindrical root member having threaded bores and having a die threaded exterior for threadedly entering a jaw bone cavity,
   a root member stabilizing bar projecting through one of the root member threaded bores for entering a patient's jaw bone adjacent the jaw bone cavity;

a prothesis having a base cooperatively received by the root member socket; and, anchor means including a first screw in another of the root member threaded bores for securing the prothesis to said root member.

2. A dental implant according to claim 1 and further including;

an eccentrically bored and counterbored substantially cylindrical implant abutment and interposed between said root member and said prothesis base.

3. A dental implant according to claim 2 in which the anchor means further includes:

a lock screw in said implant abutment for precluding angular rotation of said first screw.

4. A dental implant for a prothesis, comprising:

a substantially cylindrical root member externally die threaded for threadedly entering a jaw bone cavity having one end portion forming an upwardly open socket and an eccentric upwardly open threaded bore and having a throughbore angularly inclined with respect to its longitudinal axis;

a root member stabilizing bar projecting through the root member angularly inclined bore for entering a patient's jaw bone adjacent the jaw bone cavity; a prothesis having a base cooperatively received by the root member socket;

an eccentrically bored and counterbored substantially cylindrical implant abutment interposed between said root member and said prothesis base; and, anchor means including a first screw in the root member threaded bore for securing the prothesis to said root member.

5. A dental implant according to claim 4 in which the anchor means further includes:

a lock screw in said implant abutment for precluding angular rotation of said first screw.

6. A dental implant for a prothesis, comprising:

a substantially cylindrical root member externally die threaded for threadedly entering a jaw bone cavity having one ned portion forming an upwardly open socket and an eccentric upwardly open threaded bore and having a through bore angularly inclined at an acute angle with respect to its longitudinal axis;

a root member stabilizing bar secured in and projecting through the root member angularly inclined bore for entering a patient's jaw bone adjacent the jaw bone cavity;

a prothesis having a base cooperatively received by the root member socket;

an eccentrically bored and counterbored substantially cylindrical implant abutment interposed between said root member and said prothesis base; and, anchor means including a first screw in the root member threaded bore for securing the prothesis to said root member.

7. A dental implant according to claim 6 in which the anchor means further includes:

a lock screw in said implant abutment for precluding angular rotation of said first screw.

* * * * *